S. NORTH.
EAR TRUMPET.
No. 10,266. Reissued Jan. 9. 1883.
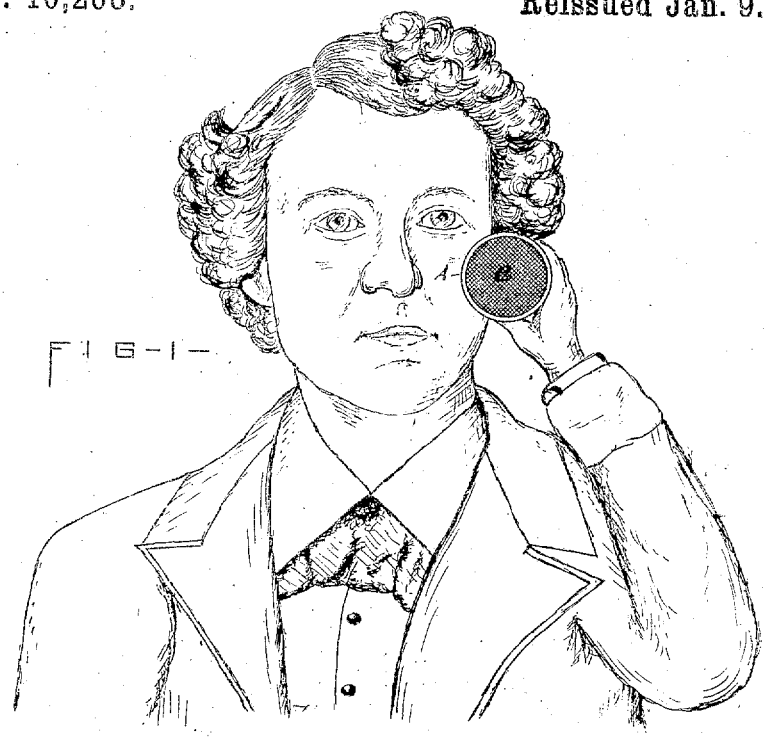
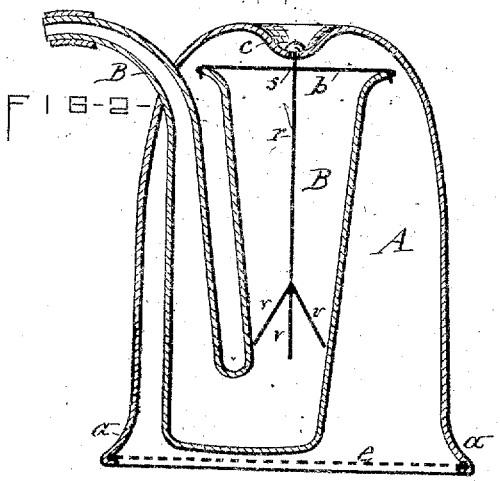
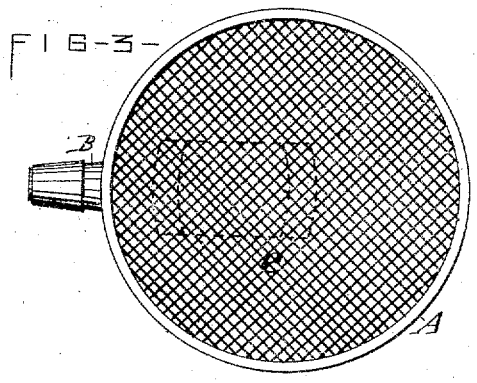
WITNESSES—
Chas. E. Raymond
C. M. Smith
INVENTOR—
Stephen North
per Dull, Laass & Hop
Attorneys

UNITED STATES PATENT OFFICE.

STEPHEN NORTH, OF SYRACUSE, NEW YORK.

EAR-TRUMPET.

SPECIFICATION forming part of Reissued Letters Patent No. 10,268, dated January 9, 1883.

Original No. 227,178, dated May 4, 1880. Application for reissue filed November 7, 1882.

*To all whom it may concern:*

Be it known that I, STEPHEN NORTH, of Syracuse, in the county of Onondaga, in the State of New York, have invented new and useful Improvements in Aural Instruments, (not patented to me, nor with my knowledge or consent in any foreign country,) of which the following, taken in connection with the accompanying drawings, is a full, clear, and exact description.

The invention relates to a novel, simple, compact, convenient, and effective instrument which I have denominated the "earphone," the same being designed to audibly convey sounds to the ear of a person of defective hearing.

The invention consists essentially of a peculiar-shaped resonant sound-receiving shell adapted to rest against the cheek of the person using the same, and having within it a tube arranged with one end in proximity to the reverberating end of the aforesaid shell, and with the opposite end projecting through the shell and adapted to be inserted in the ear of a person, by which arrangement a compact and convenient instrument is obtained which is capable of transmitting sounds audibly to a person defective of the sense of hearing.

The invention also consists in the combination, with the aforesaid instrument, of certain devices for allaying or moderating the jars or vibrations of the sound in transmission, and thus rendering the same more distinctly audible to the person using the instrument, all as hereinafter more fully described, and specifically set forth in the claims.

In the accompanying drawings, Figure 1 illustrates the method of applying my invention for use. Fig. 2 is a vertical transverse section of my earphone, and Fig. 3 an inverted plan view of the same.

Similar letters of reference indicate corresponding parts.

A represents the sound-receiving shell, made in the form of a bell having a nearly or quite straight body, terminating with a slight outward flare, as shown at *a*, at the open end of the shell, the object of this peculiar outline of said shell being to bring the same to bear against the cheek-bone when the transmitting-tube, hereinafter described, is inserted into the ear, thereby subjecting to the vibrations of the shell the nerve which extends across the cheek and to the interior of the ear.

The crown or main reverberating part of the shell A is depressed, as shown at *c*, for the purpose of deflecting the sound and throwing the same directly into the flaring mouth of a tube, B, the main portion of which is located within the shell A, and has its aforesaid mouth or receiving end facing the depression *c*, and its opposite end protruding through the shell near the crown thereof and adapted to be inserted in the ear of a person, and at the same time allow the shell to bear on the cheek, as aforesaid. Across the mouth of the tube is spanned a detonating-plate or drum-head, *b*, having a central aperture, *s*, through which passes a wire, *r*, pendent from the depression *c* of the shell, and terminating within the tube B, with a furcation or a number of prongs, *v*, the function of said wire being to break or moderate the jars or vibrations of the transmitted sound.

Across the open end of the case A is spanned a sound refining or disseminating screen, in the form of a wire-netting or other suitable finely-perforated diaphragm, *e*, which tends to further moderate the aforesaid injurious effects, and also serves to protect the inclosed transmitting and toning wire *r*.

Having thus described my invention, what I claim as new, and desire to secure by Letters Patent, is—

1. In an aural instrument, the combination of a resonant shell of bell form and with a flaring open end, and a sound-transmitting tube arranged within the said shell and with its receiving end facing the crown thereof, and having its delivery end protruding through the side of the shell and adapted to be inserted in the ear of the user of the instrument, substantially as described and shown.

2. The combination of the bell-shaped shell A, provided with the flare *a*, the tube B, situated inside of said shell, and having its receiving end facing the crown thereof and its delivery end protruding through the side of the shell, and the screen *e*, extended across the open end of the shell, all as shown and described.

3. The combination, with the resonant shell A, of the transmitting-tube B, provided with the drum-head *b*, as and for the purpose set forth.

4. The combination of the resonant shell A, having the depression *c*, and the tube B, arranged opposite the said depression, substantially in the manner shown.

5. The combination, with the shell A and tube B, of the furcated wire *r*, substantially as and for the purpose specified.

6. The combination of the shell A, provided with the netting or screen *e* and with the depression *c*, the tube B, arranged within the shell A, and having one end directly opposite the depression *c*, and provided with a drum-head, *b*, having a central aperture, *s*, the opposite end of the tube protruding through the shell and adapted for application to the ear, and the furcated wire *r*, extended from the crown of the shell A into the aforesaid tube, all constructed and combined substantially in the manner and for the purpose specified.

In testimony whereof I have hereunto signed my name and affixed my seal, in the presence of two attesting witnesses, at Syracuse, in the county of Onondaga and State of New York, this 2d day of November, 1882.

STEPHEN NORTH. [L. S.]

Witnesses:

WM. C. RAYMOND,

FREDERICK P. FISH.